US010165161B2

(12) United States Patent
Wei et al.

(10) Patent No.: US 10,165,161 B2
(45) Date of Patent: Dec. 25, 2018

(54) BRACKET ASSEMBLY FOR MOBILE TERMINAL AND MOBILE TERMINAL (71) Applicant: GUANGDONG OPPO MOBILE TELECOMMUNICATIONS CORP., LTD., Dongguan, Guangdong (CN)

(72) Inventors: Yi Wei, Dongguan (CN); Yong Li, Dongguan (CN); Peiju Chen, Dongguan (CN)

(73) Assignee: GUANGDONG OPPO MOBILE TELECOMMUNICATIONS CORP., LTD., Dongguan, Guangdong (CN)

( * ) Notice: Subject to any disclaimer, the term of this patent is extended or adjusted under 35 U.S.C. 154(b) by 0 days.

(21) Appl. No.: 15/793,588

(22) Filed: Oct. 25, 2017

(65) Prior Publication Data
US 2018/0176426 A1 Jun. 21, 2018

(30) Foreign Application Priority Data

Dec. 20, 2016 (CN) .......................... 2016 1 1185479

(51) Int. Cl.
| H04N 5/225 | (2006.01) |
| G06F 1/16 | (2006.01) |
| A61B 3/15 | (2006.01) |
| H04M 1/02 | (2006.01) |
| H04M 1/725 | (2006.01) |

(52) U.S. Cl.
CPC .......... *H04N 5/2252* (2013.01); *A61B 3/154* (2013.01); *G06F 1/1626* (2013.01); *H04M 1/026* (2013.01); *H04N 5/2254* (2013.01); *H04M 1/0264* (2013.01); *H04M 1/7258* (2013.01); *H04N 5/2257* (2013.01)

(58) Field of Classification Search
CPC .. H04N 5/2252; H04N 5/2254; H04N 5/2257; H04M 1/026; H04M 1/0264
USPC .......................................... 348/374
See application file for complete search history.

(56) References Cited

U.S. PATENT DOCUMENTS

| 9,759,988 B2 | 9/2017 | Rammah et al. |
| 2014/0111684 A1 | 4/2014 | Corbin et al. |
| 2015/0062419 A1 | 3/2015 | Hooton et al. |
| 2018/0176346 A1* | 6/2018 | Wei ..................... H04M 1/0249 |

(Continued)

FOREIGN PATENT DOCUMENTS

| CN | 201995193 U | 9/2011 |
| CN | 202750132 U | 2/2013 |
| CN | 105356077 A | 2/2016 |

(Continued)

*Primary Examiner* — Usman A Khan
(74) *Attorney, Agent, or Firm* — Ladas & Parry LLP (57) ABSTRACT A bracket assembly for use in a mobile terminal includes a metal support and a multi-contact spring. The metal support is configured to support an electronic component of the mobile terminal. The multi-contact spring includes a first pressure contact part, a second pressure contact part, a first elastic part, a second elastic part, and a fixing part. The multi-contact spring is fixed to a frame of the mobile terminal by a fastener extending through the fixing part into the frame. The first elastic part is connected to the first pressure contact part and the fixing part and is configured to provide a first restoring force to the first pressure contact part such that the first pressure contact part abuts against a metal cover of the mobile terminal and is grounded.

20 Claims, 5 Drawing Sheets (56) References Cited

U.S. PATENT DOCUMENTS

2018/0176351 A1\* 6/2018 Wei ...................... H04N 5/2257

FOREIGN PATENT DOCUMENTS

| CN | 205609765 U | 9/2016 |
|----|-------------|--------|
| WO | 2016032561 A1 | 3/2016 |

\* cited by examiner

BRACKET ASSEMBLY FOR MOBILE TERMINAL AND MOBILE TERMINAL

CROSS REFERENCE TO RELATED APPLICATION

This application claims priority to Chinese Application No. 201611185479.6 filed Dec. 20, 2016. The entire disclosure of the above application is incorporated herein by reference in its entirety.

BACKGROUND

Field

The present disclosure relates to the field of electronic equipment, and particularly to a bracket assembly for a mobile terminal and a mobile terminal having the bracket assembly.

Background

Widespread and growing use of smart phones increases the need for a support to stabilize electronic components, such as a camera device, inside a mobile phone. In consideration of rigidity, size, and installation requirements of the support, a metal support is usually used to stabilize the electronic component. However, because metal is conductive, the metal support easily interferes with electromagnetic signals from communication elements inside the mobile phone, and thus reducing communication performance of the communication elements inside the mobile phone.

In present technology, the metal support, used to stabilize the electronic component inside the mobile phone, reduces user experience.

BRIEF DESCRIPTION OF THE DRAWINGS

In order to more clearly illustrate the embodiments of the present disclosure or related art, the following figures described in the embodiments are briefly introduced. It is obvious that the drawings are merely some embodiments of the present disclosure, a person skilled in the art can obtain other figures according to these figures without paying the premise.

DETAILED DESCRIPTION OF ILLUSTRATED EMBODIMENTS

In combination with the drawings of the embodiments of the present disclosure, the following is related to a detailed and complete description of the technology of the embodiments of the present disclosure. It is obvious that the disclosed embodiments are only a part of the embodiments available to the present disclosure, rather than the all embodiments thereof. Based on the disclosed embodiments of the present disclosure, other embodiments obtained by a person skilled in the art without endeavor of creativity belong to the protected scope of the present embodiments of the present disclosure.

Referring to FIGS. 1, 2, and 3A to 3C, a bracket assembly is disposed in a mobile terminal, and the mobile terminal includes a communication element for receiving or transmitting a signal. The communication element may be a board 30 or an antenna. The bracket assembly includes a metal support 10 and a multi-contact spring 20. The metal support 10 is configured to support an electronic component of the mobile terminal. The electronic component is, for example, a dual camera assembly. The multi-contact spring 20 includes at least one first pressure contact part 201, at least one second pressure contact part 202, at least one first elastic part 203, at least one second elastic part 204, and at least one fixing part 200. The multi-contact spring 20 is fixed to a frame 40 of the mobile terminal by the at least one fixing part 200. The at least one first elastic part 203 is connected to the at least one first pressure contact part 201 and the at least one fixing part 200 and is configured to provide a first restoring force to the at least one first pressure contact part 201 such that the at least one first pressure contact part 201 firmly abuts against a metal cover 60 of the mobile terminal. The at least one second elastic part 204 is connected to the at least one second pressure contact part 202 and the at least one fixing part 200 and is configured to provide a second restoring force to the at least one second pressure contact part 202 such that the at least one second pressure contact part 202 firmly abuts against the metal support 10. The metal support 10 is connected to the metal cover 60 via the multi-contact spring 20 and is grounded. The frame 40 may be a middle frame of the mobile terminal, and the metal cover 60 may be a metal back cover of the mobile terminal. In an embodiment, the mobile terminal may be an electronic equipment such as a mobile phone, a notebook computer, a tablet computer, etc.

The fixing part 200 of the multi-contact spring 20 is stably fixed to the frame 40, the first pressure contact part 201 firmly abuts against the metal cover 60, and the second pressure contact part 202 firmly abuts against the metal support 10, such that the metal support 10 is electrically connected to the metal cover 60. The metal cover 60 is grounded, and the metal support 10 is in communication with a ground electrode of the metal cover 60 without changing mounting structure of the metal support 10 so that the overall electric potential of the metal support 10 is reduced, to improve interference with electromagnetic signals from the communication element and thus increase user experience.

Further, the multi-contact spring 20 connects current of the metal support 10 to the ground electrode of the metal cover 60. The multi-contact spring 20 can, on the one hand, reduce the overall electric potential of the metal support 10 and, on the other hand, static electricity of the metal support 10 is guided to the ground electrode so as to prevent the static electricity of the metal support 10 from flowing to the electronic component, to protect the electronic component. The ground electrode may be exposed copper on the board 30. The metal cover 60 is in communication with the board 30, and the first pressure contact part 201 of the multi-contact spring 20 abuts against the metal cover 60 to communicate with the exposed copper of the board 30.

Figure 1:
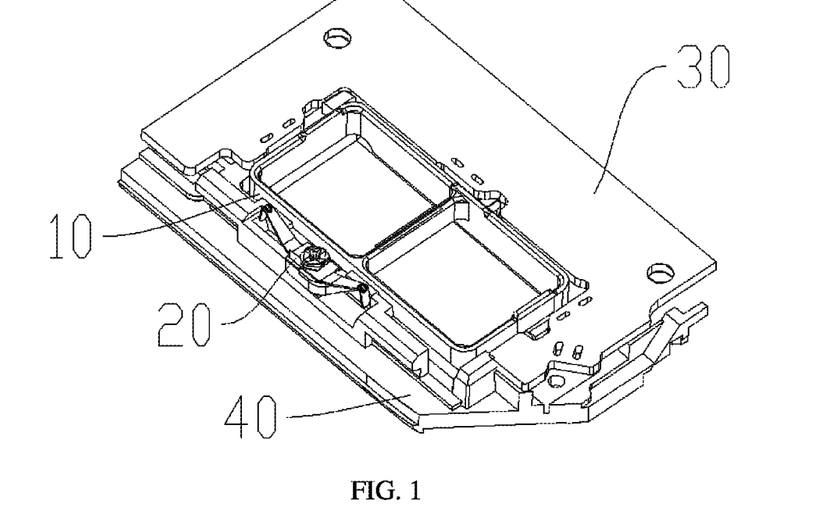
FIG. 1 is an assembled view of a bracket assembly according to an embodiment of the present disclosure.
Figure 2:
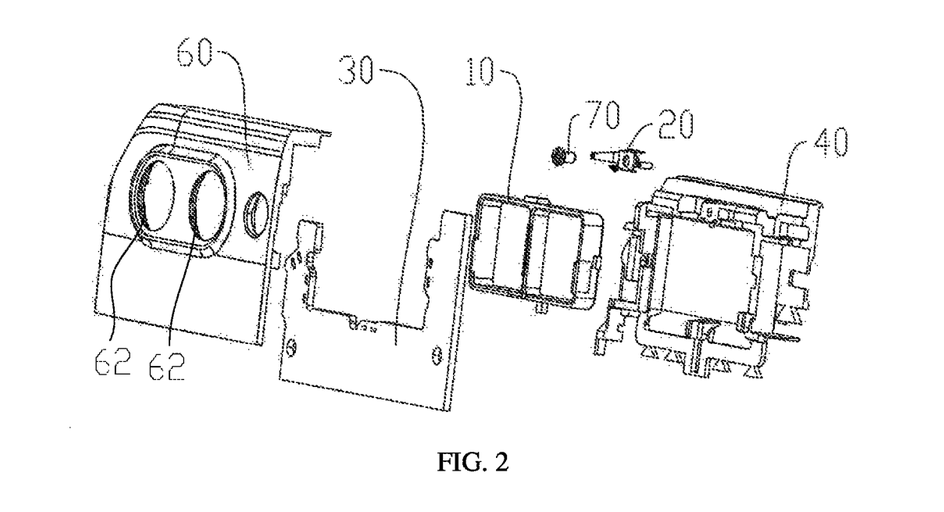
FIG. 2 is an exploded view of the bracket assembly according to the embodiment of the present disclosure.
Figure 3A:
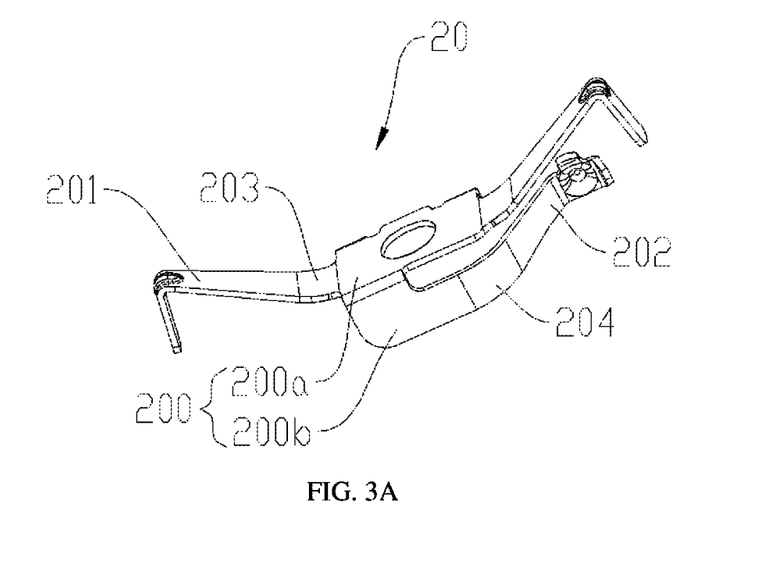
FIGS. 3A, 3B, and 3C are schematic views of a multi-contact spring according to the embodiment of the present disclosure.
Figure 3B:
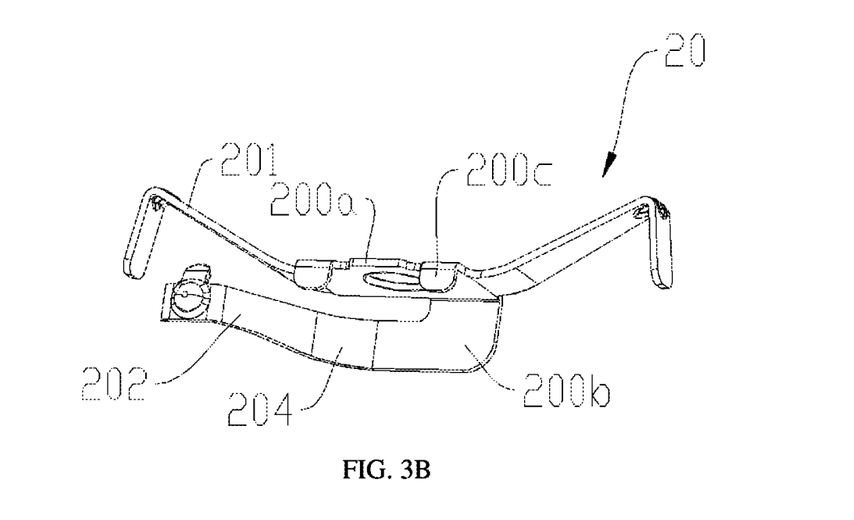
Figure 3C:
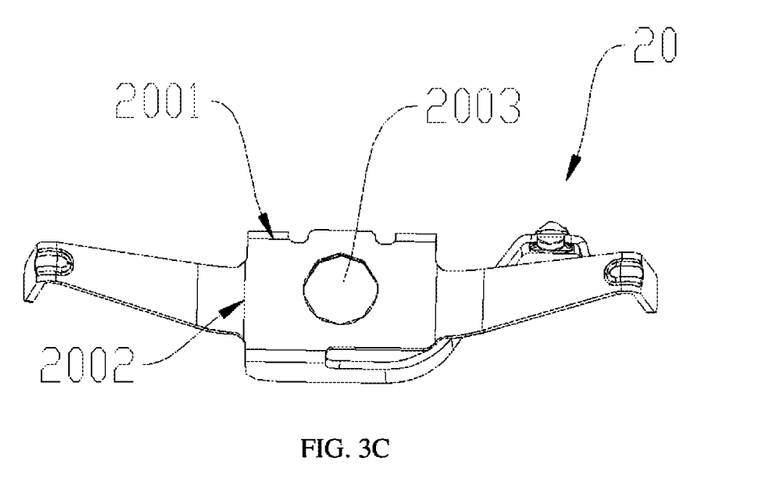

In an embodiment, the at least one fixing part 200 includes a base piece 200a having a pair of long sides 2001 and a pair of short sides 2002 connecting the long sides 2001. The at least one first pressure contact part 201 is elastically connected to the short sides 2002 by the at least one first elastic part 203, the base piece 200a extends along one of the long sides 2001 and is bent to form a connecting piece 200b, and the at least one second pressure contact part 202 is elastically connected to the connecting piece 200b by the at least one second elastic part 202. In an embodiment, the base piece 200a is a long strip, the pair of long sides 2001 are parallel to each other, and the pair of short sides 2002 are parallel to each other. The first pressure contact part 201 is elastically connected to an edge of the short side 2002 by the first elastic part 203. The first elastic part 203 applies an elastic force to the first pressure contact part 201, and when the first pressure contact part 201 is subjected to pressure opposite to a direction of the elastic force provided by the first elastic part 203, the first elastic part 203 causes the first pressure contact part 201 to firmly abuts against an object, which applies pressure to the first pressure contact part 201. In the embodiment, the object for applying pressure to the first pressure contact part 201 may be the metal cover 60. One of the long sides 2001 of the base piece 200a extends and is bent to form the connecting piece 200b. The connecting piece 200b is at an angle to the base piece 200a. For example, the connecting piece 200b and the base piece 200a are perpendicular to each other. The connecting piece 200b is connected to the second pressure contact part 202 and the fixing part 200. In detail, the second pressure contact part 202 is elastically connected to the connecting piece 200b by the second elastic part 204. The second elastic part 204 applies an elastic force to the second pressure contact part 202, and when the second pressure contact part 202 is subjected to pressure opposite to a direction of the elastic force provided by the second elastic part 204, the second elastic part 204 causes the second pressure contact part 202 to firmly abuts against an object, which applies pressure to the second pressure contact part 202. In the embodiment, the object for applying pressure to the second pressure contact part 202 may be the metal support 10.

The fixing part 200 of the multi-contact spring 20 is stably fixed to the frame 40, the first pressure contact part 201 firmly abuts against the metal cover 60, and the second pressure contact part 202 firmly abuts against the metal support 10, such that the metal support 10 is electrically connected to the metal cover 60. The metal cover 60 is grounded, and the metal support 10 is in communication with the ground electrode of the metal cover 60 without changing the mounting structure of the metal support 10 so that the overall electric potential of the metal support 10 is reduced to improve interference with electromagnetic signals from the communication element and thus increase user experience.

Further, a number of the at least one first pressure contact part 201 is two, a number of the at least one first elastic part 203 is two, and each of the first pressure contact parts 201 is elastically connected to one of the short sides 2002 by a respective one of the first elastic parts. The two first pressure contact parts 201 abut against a housing of the mobile terminal such that the metal support 10 is grounded, a number of contacts is increased, the overall electric potential of the metal support 10 is reduced, and interference of electromagnetic signals from the communication elements is reduced.

Figure 4:
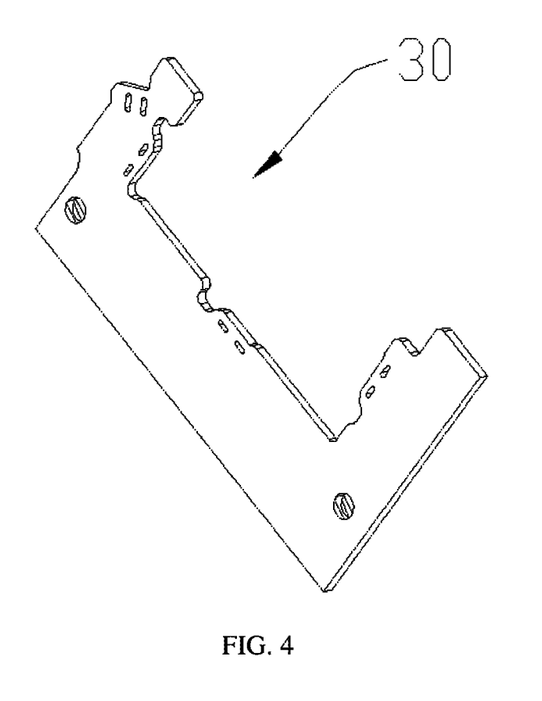
FIG. 4 is a schematic view of a board according to the embodiment of the present disclosure.

Referring to FIGS. 3 and 4, in the embodiment, the bracket assembly includes a fastener 70, the base piece 200a includes a fixing hole 2003, and the frame 40 includes a convex part 400 having a threaded hole 402 configured to fix the multi-contact spring 20 to the convex part 400 by the fastener 70. In an embodiment, the fastener 70 may be a screw. The base piece 200a is locked to the frame 40 by the screw such that the multi-contact spring 20 is securely fixed to the frame 40. Therefore, the first pressure contact part 201 can stably abut against the metal cover 60, the second pressure contact part 202 can stably abut against the metal support 10, and structural stability of the bracket assembly is improved.

In addition, the base piece 200a extends along another of the long sides 2001 and is bent to form a plurality of bending ends, a bending direction of the bending ends with respect to the base piece 200a is the same as a bending direction of the connecting piece 200b. The bending ends, the base piece 200a, and the connecting piece 200b are connected in order, the base piece 200a includes a receiving space defined by a region among the bending ends, the base piece 200a, and the connecting piece 200b. The convex part 400 of the frame 40 is received in the receiving space to restrict rotation of the multi-contact spring 20. In another embodiment, a number of the bent ends of each of the multi-contact spring 20 is two for firmly fixing the multi-contact spring 20 and the frame 40.

Figure 5:
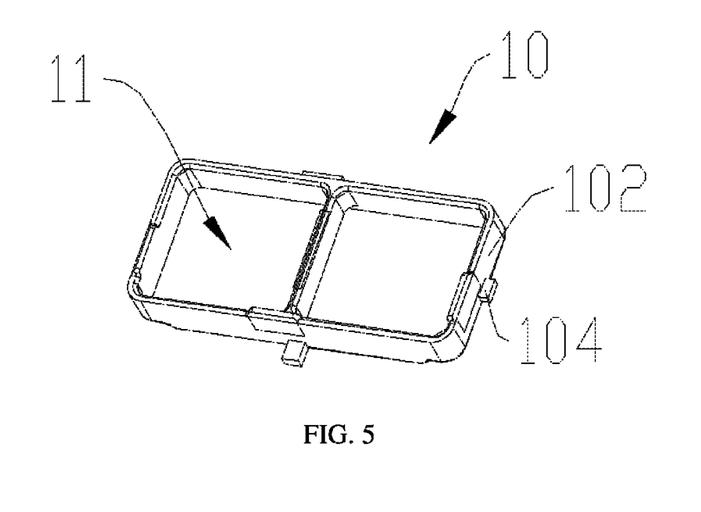
FIG. 5 is a schematic view of a metal support according to the embodiment of the present disclosure.

Referring to FIG. 5, in the embodiment, the metal support 10 includes a plurality of side walls 102 connected in order and an accommodating space 11 cooperatively defined by the side walls 102 for accommodating the electronic component. In detail, the metal support 10 accommodates the electronic component to facilitate installation and stabilization of the electronic component. The electronic component may be a camera module, a speaker, a fingerprint module, a connector, etc.

Further, the metal support 10 has a rectangular block shape. The metal support 10 may be made of aluminum alloy material, silver material, or iron material, etc. The metal support 10 is formed by shaping a metal block using an automatic numerical control milling process. That is, forming dimensions of the side walls 102 are machined by the numerical control milling process such that dimensional accuracy of the side wall 102 is high, the electronic component can be effectively stabilized and precisely positioned, and the position of the electronic component can be easily calibrated. In addition, the metal support 10 can also be effectively fixed to an external member such that the fixing position of the metal support 10 is precise and the metal support 10 is conveniently positioned. Therefore, the mounting position of the electronic component can be accurately improved and performance of the electronic component can be improved. The accommodating space 11 can accommodate one electronic component, two electronic components, or a plurality of electronic components such that the metal support 10 can fix the plurality of electronic components centrally to save space.

In the embodiment, the side walls 102 include a wall away from a side of the accommodating space 11, and a pressure contact part (including the first pressure contact part 201 and the second pressure contact part 202) elastically abuts against the wall. Restoring force applied to the pressure contact part by an elastic part (including the first elastic part 203 and the second elastic part 204) causes the pressure contact part to firmly abut against the wall of the side wall 102 of the metal support 10 to ensure that the pressure contact part and the metal support 10 can be brought into stable contact. Therefore, loose contact between the multi-contact spring 20 and the metal support 10 does not occur easily when using the mobile terminal, and the structural stability of the mobile terminal is improved. In addition, the pressure contact part elastically contacts the wall of the metal support 10 to facilitate installation and removal of the metal support 10. The metal support 10 is removed from the mobile terminal by simply pulling out the metal support 10 in a direction perpendicular to the pressure contact part against the side wall 102. The metal support 10 is mounted on the mobile terminal by simply pushing the pressure contact part in advance and placing the metal support 10 in the mobile terminal. The difficulty of installation and removal of the metal support 10 is reduced.

Figure 6:
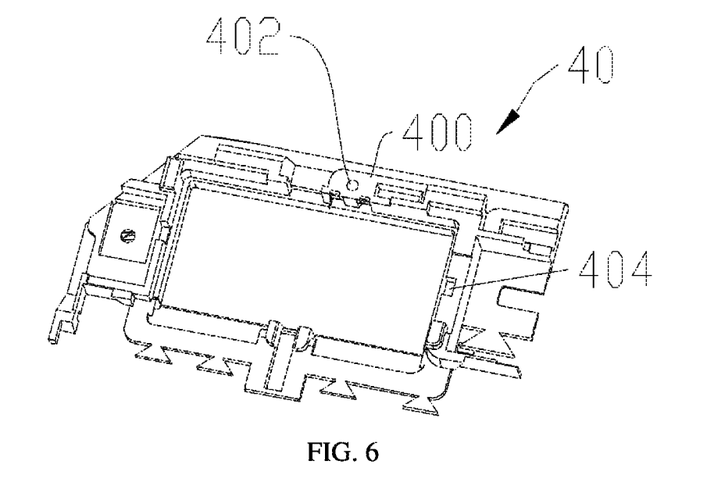
FIG. 6 is a schematic view of a frame according to the embodiment of the present disclosure.

Referring to FIG. 6, in the embodiment, the bracket assembly is applied to the mobile terminal, and the metal support 10 is fixed to the frame 40. In detail, the wall away from a side of the accommodating space 11 includes a plurality of fixing blocks 104 convexly disposed on the wall. The frame 40 includes a plurality of slots 404 corresponding to the fixing blocks 104 for inserting the fixing blocks 104 such that the metal support 10 is mounted on the frame 40. The fixing blocks 104 of the metal support 10 engage with the slots 404 such that the metal support 10 is securely mounted on the frame 40 to improve structural stability of the mobile terminal.

In the embodiment, the bracket assembly includes a plurality of convex contacts disposed on a top of the pressure contact part, and the convex contacts increases a contact area between the pressure contact part and the metal support 10, such that the pressure contact part firmly abuts against the side wall 102 of the metal support 10.

In the embodiment, the first pressure contact part 201, the second pressure contact part 202, the first elastic part 203, the second elastic part 204, and the fixing part 200 are an integral structure integrally formed by bending at least one of a metal material and a metal alloy material. Therefore, manufacturing process of the elastic device is simplified and production materials of the elastic device is saved.

The fixing part 200 of the multi-contact spring 20 is stably fixed to the frame 40, the first pressure contact part 201 firmly abuts against the metal cover 60, and the second pressure contact part 202 firmly abuts against the metal support 10, such that the metal support 10 is electrically connected to the metal cover 60. The metal cover 60 is grounded, and the metal support 10 is in communication with a ground electrode of the metal cover 60 without changing a mounting structure of the metal support 10 so that the overall electric potential of the metal support 10 is reduced to improve interference with electromagnetic signals from the communication element and thus increase user experience.

Figure 7:
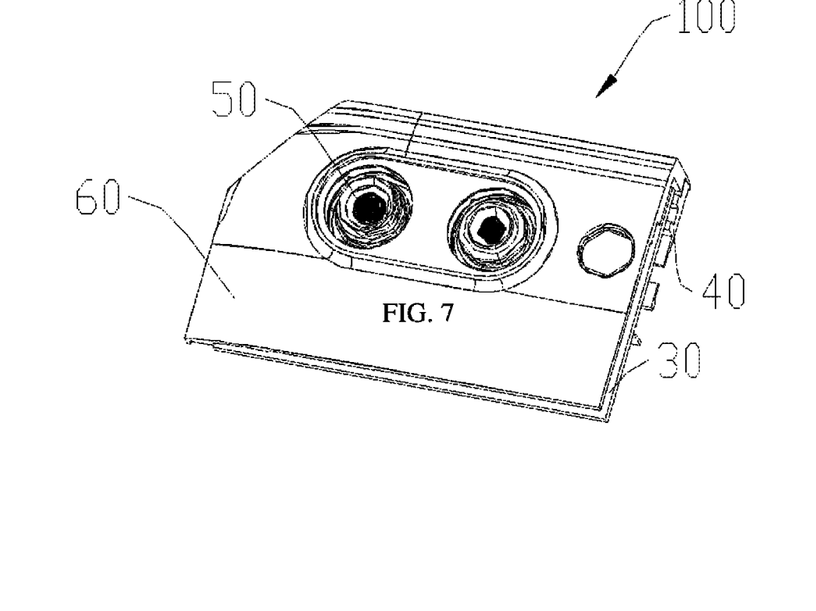
FIG. 7 is a partially assembled view of a mobile terminal according to the embodiment of the present disclosure.
Figure 8:
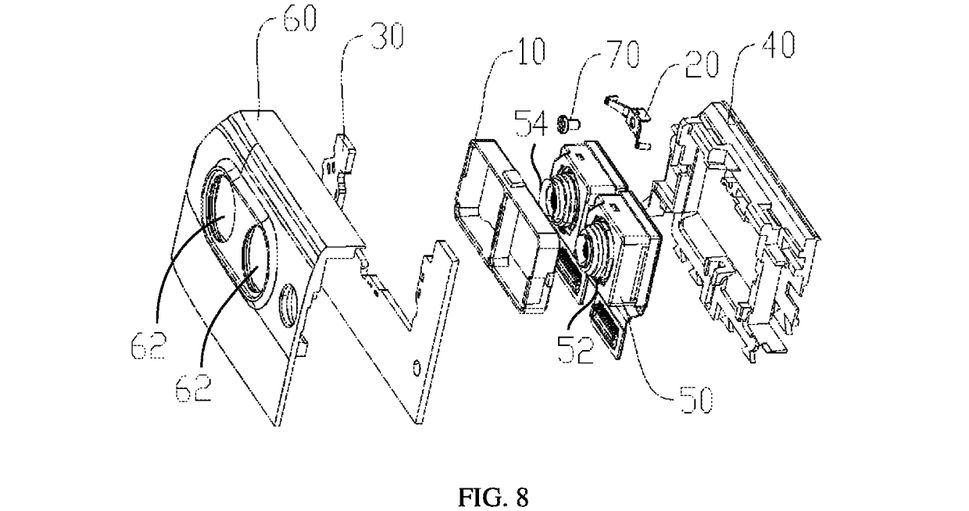
FIG. 8 is a partially exploded view of the mobile terminal according to the embodiment of the present disclosure.

Referring to FIGS. 7 and 8, an embodiment of the disclosure includes a mobile terminal 100. The mobile terminal 100 includes the metal cover 60, the board 30, the frame 40, and the bracket assembly. The multi-contact spring 20 is fixed to the frame 40, the first pressure contact part abuts against the grounded metal cover 60. The board 30 includes a ground electrode. The metal cover 60 is connected to the board 30. The second pressure contact part abuts against the metal support 10 to ground the metal support 10. The multi-contact spring 20 is fixed to the frame 40 of the mobile terminal 100 by the at least one fixing part 200. The at least one first elastic part 203 is connected to the at least one first pressure contact part 201 and the at least one fixing part 200 and is configured to provide a first restoring force to the at least one first pressure contact part 201 such that the at least one first pressure contact part 201 firmly abuts against the metal cover 60 of the mobile terminal 100.

The at least one second elastic part 204 is connected to the at least one second pressure contact part 202 and the at least one fixing part 200 and is configured to provide a second restoring force to the at least one second pressure contact part 202 such that the at least one second pressure contact part 202 firmly abuts against the metal support 10. The metal support 10 is connected to the metal cover 60 via the multi-contact spring 20 and is grounded. The overall electric potential of the metal support 10 is reduced to improve interference with electromagnetic signals from the communication element and thus increase user experience.

The metal support 10 is configured to support an electronic component of the mobile terminal 100. The electronic component is for example a dual camera assembly 50. The electronic component includes a first camera lens 52 and a second camera lens 54 arranged side by side with the first camera lens 52, and the first camera lens 52 and the second camera lens 54 are disposed in the accommodating space 11 of the metal support 10. In detail, an image optical axis of the first camera lens 52 and an image optical axis of the second camera lens 54 are parallel such that the first camera lens 52 and the second camera lens 54 can be operated in concert to improve picture taking performance.

In the embodiment, the frame 40 is used to fix the metal support 10. In detail, the wall away from a side of the accommodating space 11 includes a plurality of fixing blocks 104 convexly disposed on the wall. The frame 40 includes a plurality of slots 404 corresponding to the fixing blocks 104 for inserting the fixing blocks 104 such that the metal support 10 is mounted on the frame 40. The fixing blocks 104 of the metal support 10 engage with the slots 404 such that the metal support 10 is securely mounted on the frame 40 to improve structural stability of the mobile terminal.

In the embodiment, the metal cover 60 is attached to the frame 40, and the board 30 is fixed between the metal cover 60 and the frame 40 for covering and protecting the electronic component inside the mobile terminal 100, and thus increasing appearance of the mobile terminal 100. The metal cover 60 may be a metal plate. Further, the metal cover 60 includes two shooting windows, and the first camera lens 52 and the second camera lens 54 take pictures through a respective window of the two shooting windows 62 to realize picture taking. In the embodiment, the shooting window 62 is a camera lens.

The fixing part 200 of the multi-contact spring 20 is stably fixed to the frame 40, the first pressure contact part 201 firmly abuts against the metal cover 60, and the second pressure contact part 202 firmly abuts against the metal support 10, such that the metal support 10 is electrically connected to the metal cover 60. The metal cover 60 is grounded, and the metal support 10 is in communication with a ground electrode of the metal cover 60 without changing a mounting structure of the metal support 10 so that the overall electric potential of the metal support 10 is reduced to improve interference with electromagnetic signals from the communication element and thus increase user experience.

The foregoing descriptions are merely exemplary embodiments of the present disclosure, rather than limiting the present disclosure. Various modifications and alterations may be made to the present disclosure for a person skilled in the art. Any modification, equivalent substitution, improvement or the like made within the spirit and principle of the present disclosure shall fall into the protection scope of the present disclosure.

What is claimed is:

1. A bracket assembly in a mobile terminal, the mobile terminal comprising a communication element, an electronic component, a frame, and a metal cover, the bracket assembly comprising:
   a metal support configured to support the electronic component of the mobile terminal; and
   a multi-contact spring comprising at least one first pressure contact part, at least one second pressure contact part, at least one first elastic part, at least one second elastic part, and at least one fixing part, wherein the multi-contact spring is fixed to the frame of the mobile terminal by the at least one fixing part, the at least one first elastic part is connected to the at least one first pressure contact part and the at least one fixing part and is configured to provide a first restoring force to the at least one first pressure contact part such that the at least one first pressure contact part abuts against the metal cover of the mobile terminal and is grounded, and the at least one second elastic part is connected to the at least one second pressure contact part and the at least one fixing part and is configured to provide a second restoring force to the at least one second pressure contact part such that the at least one second pressure contact part abuts against the metal support so as to ground the metal support to reduce signal interference of the metal support to the communication element.

2. The bracket assembly as claimed in claim 1, wherein the at least one fixing part comprises a base piece having a pair of long sides and a pair of short sides connecting the long sides, the at least one first pressure contact part is elastically connected to the short sides by the at least one first elastic part, the base piece extends along one of the long sides and is bent to form a connecting piece, and the at least one second pressure contact part is elastically connected to the connecting piece by the at least one second elastic part.

3. The bracket assembly as claimed in claim 2, wherein a number of the at least one first pressure contact part is two, a number of the at least one first elastic part is two, and each of the first pressure contact parts is elastically connected to one of the short sides by a respective one of the first elastic parts.

4. The bracket assembly as claimed in claim 3, wherein the mobile terminal comprises a fastener, and the base piece comprises a fixing hole configured to insert the fastener to fix the multi-contact spring to the frame.

5. The bracket assembly as claimed in claim 4, wherein the frame comprises a convex part, the base piece extends along another of the long sides and is bent to form a plurality of bending ends, a bending direction of the bending ends with respect to the base piece is the same as a bending direction of the connecting piece, the bending ends, the base piece, and the connecting piece are connected in order, the base piece comprises a receiving space defined by a region among the bending ends, the base piece, and the connecting piece, and the convex part of the frame configured to fix the multi-contact spring is received in the receiving space so as to restrict rotation of the multi-contact spring with respect to the fastener.

6. The bracket assembly as claimed in claim 1, wherein the metal support comprises a plurality of side walls connected in order and an accommodating space cooperatively defined by the side walls for accommodating the electronic component, the side walls comprises a wall away from a side of the accommodating space, and the second pressure contact part elastically abuts against the wall.

7. The bracket assembly as claimed in claim 6, wherein the frame comprises a slot, and the wall comprises a plurality of fixing blocks convexly disposed on the wall for inserting into the slot of the frame such that the metal support is mounted on the frame.

8. The bracket assembly as claimed in claim 1, further comprising a plurality of convex contacts disposed on a top of the first pressure contact part and a top of the second pressure contact part.

9. The bracket assembly as claimed in claim 1, wherein the first pressure contact part, the second pressure contact part, the first elastic part, the second elastic part, and the fixing part are an integral structure integrally formed by bending at least one of a metal material and a metal alloy material.

10. A mobile terminal, comprising:
    a communication element disposed in the mobile terminal;
    a frame;
    a metal cover, being attached to the frame;
    an electronic component; and
    a bracket assembly, comprising:
        a metal support configured to support the electronic component of the mobile terminal; and
        a multi-contact spring comprising at least one first pressure contact part, at least one second pressure contact part, at least one first elastic part, at least one second elastic part, and at least one fixing part, wherein the multi-contact spring is fixed to the frame of the mobile terminal by the at least one fixing part, the at least one first elastic part is connected to the at least one first pressure contact part and the at least one fixing part and is configured to provide a first restoring force to the at least one first pressure contact part such that the at least one first pressure contact part abuts against the metal cover of the mobile terminal and is grounded, and the at least one second elastic part is connected to the at least one second pressure contact part and the at least one fixing part and is configured to provide a second restoring force to the at least one second pressure contact part such that the at least one second pressure contact part abuts against the metal support so as to ground the metal support to reduce signal interference of the metal support to the communication element.

11. The mobile terminal as claimed in claim 10, wherein the electronic component is a dual camera assembly.

12. The mobile terminal as claimed in claim 10, wherein the at least one fixing part comprises a base piece having a pair of long sides and a pair of short sides connecting the long sides, the at least one first pressure contact part is elastically connected to the short sides by the at least one first elastic part, the base piece extends along one of the long sides and is bent to form a connecting piece, and the at least one second pressure contact part is elastically connected to the connecting piece by the second at least one elastic part.

13. The mobile terminal as claimed in claim 12, wherein a number of the at least one first pressure contact part is two, a number of the at least one first elastic part is two, and each of the first pressure contact parts is elastically connected to one of the short sides by a respective one of the first elastic parts.

14. The mobile terminal as claimed in claim 13, wherein the mobile terminal comprises a fastener, and the base piece comprises a fixing hole configured to insert the fastener to fix the multi-contact spring to the frame.

15. The mobile terminal as claimed in claim 14, wherein the frame comprises a convex part, the base piece extends along another of the long sides and is bent to form a plurality of bending ends, a bending direction of the bending ends with respect to the base piece is the same as a bending direction of the connecting piece, the bending ends, the base piece, and the connecting piece are connected in order, the base piece comprises a receiving space defined by a region among the bending ends, the base piece, and the connecting piece, and the convex part of the frame configured to fix the multi-contact spring is received in the receiving space so as to restrict rotation of the multi-contact spring with respect to the fastener.

16. The mobile terminal as claimed in claim 10, wherein the metal support comprises a plurality of side walls connected in order and an accommodating space cooperatively defined by the side walls for accommodating the electronic component, the side walls comprises a wall away from a side of the accommodating space, and the second pressure contact part elastically abuts against the wall.

17. The mobile terminal as claimed in claim 16, wherein the frame comprises a plurality of slots surrounding the metal support, and the wall comprises a plurality of fixing blocks convexly disposed on the wall for inserting into the slot of the frame such that the metal support is mounted on the frame.

18. The mobile terminal as claimed in claim 10, further comprising a plurality of convex contacts disposed on a top of the first pressure contact part and a top of the second pressure contact part.

19. The mobile terminal as claimed in claim 16, wherein the electronic component comprises a first camera lens and a second camera lens arranged side by side with the first camera lens, and the first camera lens and the second camera lens are disposed in the accommodating space.

20. The mobile terminal as claimed in claim 19, wherein the metal cover comprises two shooting windows, and the first camera lens and the second camera lens take pictures through a respective window of the two shooting windows.

* * * * *